(12) United States Patent
Shippen

(10) Patent No.: US 9,713,454 B2
(45) Date of Patent: Jul. 25, 2017

(54) DATA TRANSFER ACROSS A ROTATING BOUNDARY

(71) Applicant: Analogic Corporation, Peabody, MA (US)

(72) Inventor: Peter Daniel Shippen, Ipswich, MA (US)

(73) Assignee: ANALOGIC CORPORATION, Peabody, MA (US)

( * ) Notice: Subject to any disclaimer, the term of this patent is extended or adjusted under 35 U.S.C. 154(b) by 118 days.

(21) Appl. No.: 14/699,488

(22) Filed: Apr. 29, 2015

(65) Prior Publication Data
US 2016/0317115 A1 Nov. 3, 2016

(51) Int. Cl.
*A61B 6/03* (2006.01)
*A61B 6/00* (2006.01)
*H05K 1/14* (2006.01)
*H05K 3/36* (2006.01)

(52) U.S. Cl.
CPC ............. *A61B 6/56* (2013.01); *A61B 6/035* (2013.01); *H05K 1/142* (2013.01); *H05K 3/368* (2013.01); *H05K 2201/041* (2013.01); *H05K 2201/09018* (2013.01)

(58) Field of Classification Search
CPC ........................................................ A61B 6/56
See application file for complete search history.

(56) References Cited

U.S. PATENT DOCUMENTS

| | | | | |
|---|---|---|---|---|
| 5,530,422 A * | 6/1996 | Harrison | ................. | A61B 6/56 340/500 |
| 2007/0040635 A1* | 2/2007 | Popescu | ................. | A61B 6/035 333/261 |
| 2013/0279647 A1* | 10/2013 | Krupica | ................ | G01N 23/046 378/19 |

* cited by examiner

*Primary Examiner* — Wyatt Stoffa
*Assistant Examiner* — Eliza Osenbaugh-Stewar
(74) *Attorney, Agent, or Firm* — Cooper Legal Group, LLC

(57) ABSTRACT

A computed tomography (CT) imaging modality includes a stator and a rotor that rotates relative to the stator. The CT imaging modality includes a radiation source and a detector array for detecting at least some of the radiation. A first data communication component is coupled to the stator or the rotor for transmitting data between the stator and the rotor. The first data communication component includes a first circuit board assembly including a first conductive layer and a first dielectric layer and a second circuit board assembly including a second conductive layer and a second dielectric layer. The second conductive layer of the second circuit board assembly faces the first conductive layer of the first circuit board assembly. An insulating layer is disposed between the first conductive layer of the first circuit board assembly and the second conductive layer of the second circuit board assembly.

20 Claims, 6 Drawing Sheets

DATA TRANSFER ACROSS A ROTATING BOUNDARY

BACKGROUND

The present application relates to the transference of information over an airgap separating two members configured for relative rotation. It finds particular application in the context of computed tomography (CT) imaging applications, where at least one of a first data communication component or a second data communication component is located on a rotor and an airgap separating the first data communication component from the second data communication component is small (e.g., 20 mm or less). However, it may also apply to other applications, such as explosive detection machines, radar antennas, etc. where communication signals are wirelessly transferred.

Today, CT and other radiation imaging modalities (e.g., single-photon emission computed tomography (SPECT), mammography, projection radiography, etc.) are useful to provide information, or images, of interior aspects of an object under examination. Generally, the object is exposed to radiation comprising photons (e.g., such as x-rays, gamma rays, etc.), and an image(s) is formed based upon the radiation absorbed and/or attenuated by the interior aspects of the object, or rather an amount of photons that is able to pass through the object. Generally, highly dense aspects of the object absorb and/or attenuate more radiation than less dense aspects, and thus an aspect having a higher density, such as a bone or metal, for example, will be apparent when surrounded by less dense aspects, such as muscle or clothing.

Some radiation imaging modalities, such as CT, are configured to generate volumetric data corresponding to an object under examination. To generate this volumetric data, the CT imaging modality is typically configured to rotate a radiation source and a detector array about the object under examination (e.g., causing the object to be viewed from a plurality of angles). For example, the radiation source and/or the detector array may be mounted to a rotor, also referred to as a rotating gantry, configured for rotation relative to a stator, also referred to as a stationary unit.

Given that the radiation source and the detector array are mounted on the rotor, power and control information (e.g., instructing the radiation source and/or other electronic components how to operate) are typically supplied to the rotor from the stator. Moreover, imaging data (e.g., data generated in response to the detection of radiation by the detector array) and/or status information (e.g., indicative of a status of various components mounted to the rotor) are typically transferred from the rotor to the stator. It may be appreciated that the volume of data transferred, particularly with respect imaging data, may be quite large. For example, some imaging modalities may require transfer speeds of up to 5 gigabits per second (e.g., particularly if the rotor does not comprise a storage medium to temporarily store data until the data can be transferred).

Conventionally, slip-ring assemblies have been used to transfer power and/or information (e.g., control information, status information, and/or imaging data) between the stator and the rotor or more generally between a movable unit and a stator (or between two movable units) through the physical contact of two materials (e.g., via a sliding contact). For example, a slip-ring attached to the stator may comprise metal brushes that are configured to physically contact electrically conductive surfaces (e.g., metal brushes) comprised on a slip-ring attached to the movable unit, allowing power and/or information to be transferred between the stator and the movable unit.

While the use of slip-ring assemblies has proven effective for transferring power and/or information between a stator and a movable unit (e.g., such as a rotor) and/or between two movable units, conventional slip-ring assemblies may generate dust or particles (e.g., as metal brushes wear), may be unreliable (e.g., again as contact surfaces, such as metal brushes, wear), and/or may be noisy (e.g., as surfaces rub against one another), which may cause interference with some procedures (e.g., CT imaging). Other drawbacks of slip-ring assemblies may include cost and complexity of manufacture due to special materials and/or mechanical precision that may be required.

More recently, contactless assemblies have been devised to transfer the data (e.g., or electrical signals corresponding to the data) between the rotor and the stator. While such assemblies overcome many of the aforementioned drawbacks to a slip-ring assembly, the rotor and/or the stator may have a diameter of 5 feet or more and a contactless assembly may be disposed along a circumference of the rotor and/or stator. Given the length of these assemblies, the signal transmitted through a contactless assembly may experience a high degree of attention, which may cause signal distortion. In addition, these contactless assemblies may be more difficult to manufacture and/or may have higher manufacturing costs than conventional slip-ring assemblies.

SUMMARY

Aspects of the present application address the above matters, and others. According to one aspect, a computed tomography (CT) imaging modality comprises a stator and a rotor configured to rotate relative to the stator. The CT imaging modality comprises a radiation source coupled to the rotor and configured to emit radiation. The CT imaging modality comprises a detector array coupled to the rotor and configured to detect at least some of the radiation. The CT imaging modality comprises a first data communication component coupled to the stator or the rotor for transmitting data between the stator and the rotor. The first data communication component comprises a first circuit board assembly comprising a first conductive layer and a first dielectric layer. The first data communication component comprises a second circuit board assembly comprising a second conductive layer and a second dielectric layer. The second circuit board assembly is spaced apart from the first circuit board assembly. The second conductive layer of the second circuit board assembly faces the first conductive layer of the first circuit board assembly. An insulating layer is disposed between the first conductive layer of the first circuit board assembly and the second conductive layer of the second circuit board assembly.

According to another aspect, a data communication system for wirelessly transmitting data comprises a first circuit board assembly comprising a first conductive layer and a first dielectric layer. The first dielectric layer has a first surface in contact with the first conductive layer and a second surface substantially parallel to the first surface. A first lateral surface defines a first end of the first dielectric layer and extends between the first surface and the second surface. A first conductive edge of the first conductive layer extends from the first surface towards the second surface along the first lateral surface. A second circuit board assembly is spaced apart from the first circuit board assembly. The second circuit board assembly comprises a second conductive layer facing the first conductive layer. The second circuit board assembly comprises a second dielectric layer and an insulating layer disposed between the first conductive layer and the second conductive layer.

According to another embodiment, a data communication system for wirelessly transmitting data comprises a first circuit board assembly comprising a first conductive layer and a first dielectric layer. The data communication system comprises a second circuit board assembly comprising a second conductive layer and a second dielectric layer. The second circuit board assembly is spaced apart from the first circuit board assembly. The second conductive layer faces the first conductive layer. An insulating layer is disposed between the first conductive layer and the second conductive layer. A support structure circumferentially surrounds one or more of the first circuit board assembly, the second circuit board assembly, or the insulating layer. The support structure is configured to maintain a relative position of the first circuit board assembly, the second circuit board assembly, and the insulating layer. Those of ordinary skill in the art will appreciate still other aspects of the present application upon reading and understanding the appended description.

FIGURES

The application is illustrated by way of example and not limitation in the figures of the accompanying drawings, in which like references indicate similar elements and in which.

DESCRIPTION

Figure 1:
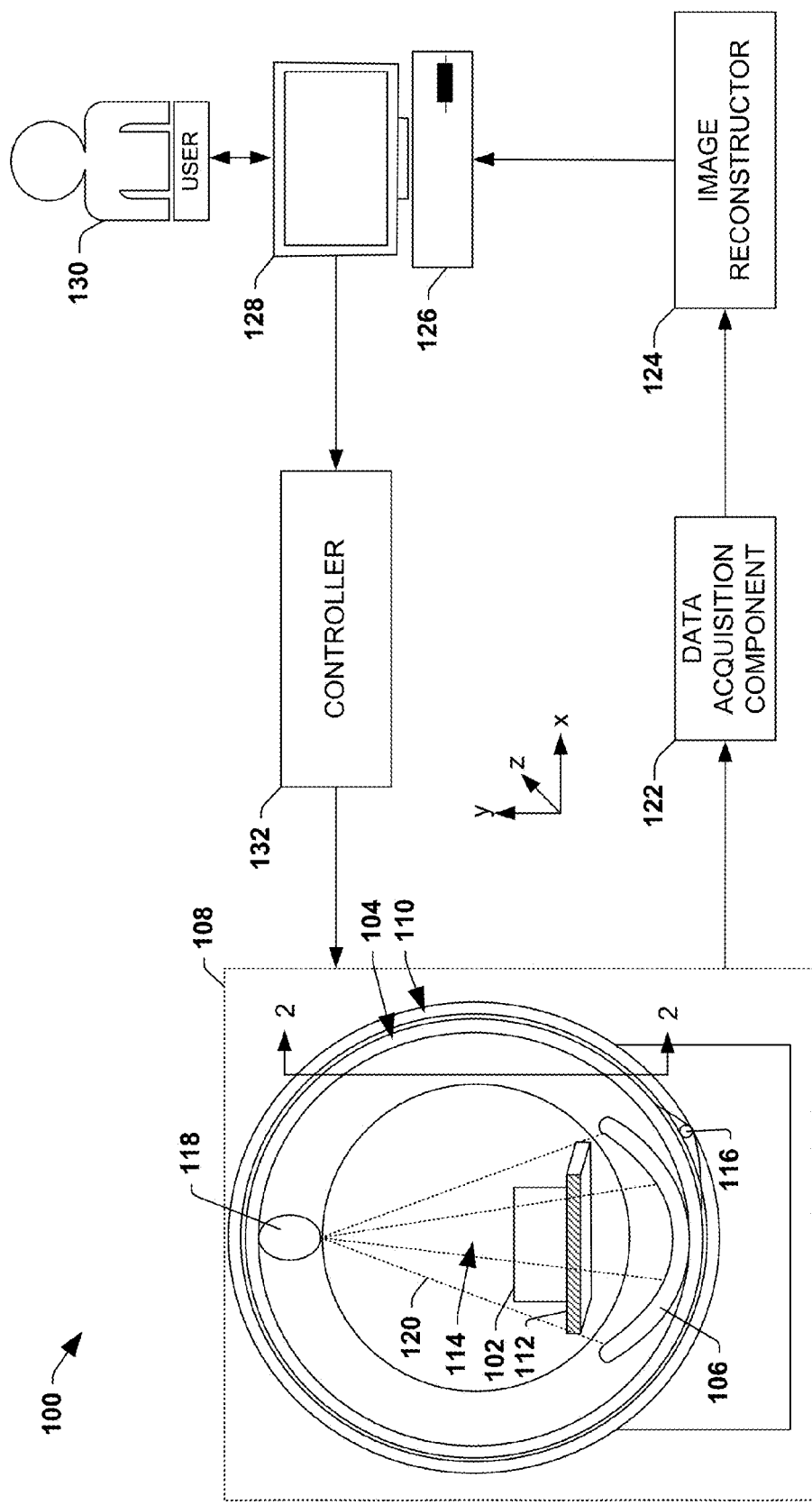
FIG. 1 is a schematic block diagram illustrating an example environment where a data communication system such as described herein may be implemented.

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

The present disclosure relates to a data communication system for transferring data and/or information between two (or more) units. Typically, at least one of the units is movable (e.g., rotating) relative to the other unit. The two units may be separated by an airgap (or gap of some other medium, material, etc.). The data communication system can comprise two or more components. For example, the data communication system can comprise a first data communi- cation component (e.g., a first antenna) that can be coupled to a stator or a rotor. The data communication system can also comprise a second data communication component (e.g., a second antenna) that can be coupled to the stator when the first data communication component is coupled to the rotor, or to the rotor when the first data communication component is coupled to the stator.

The first data communication component comprises a plurality of circuit board assemblies. For example, the first data communication component can comprise a first circuit board assembly and a second circuit board assembly that are separated by an insulating layer. The first circuit board assembly and the second circuit board assembly can be attached (e.g., end to end) to a third circuit board assembly and a fourth circuit board assembly. In this way, respective pairs of circuit board assemblies form a segment of an antenna that wraps around and/or is embedded within the rotor and/or the stator, for example.

FIG. 1 is an illustration of an example environment 100 where a data communication system as provided for herein can be useful. More particularly, FIG. 1 illustrates an example computed tomography (CT) imaging modality that can be configured to transmit data between a rotating side of the CT imaging modality and a stationary side of the CT imaging modality, including image data corresponding to an object 102 under examination.

It may be appreciated that while a CT imaging modality is described herein, the instant application is not intended to be so limited. That is, to the extent practical, the instant application, including the scope of the claimed subject matter, is intended to be applicable to other apparatuses where an antenna and/or a data communication system comprising such an antenna can be useful. More particularly, the instant application is applicable to other apparatuses where supplying communication information (e.g., control information, status information, imaging information, etc.) to and/or from a movable unit of an apparatus would be useful. Moreover, the example environment 100 merely illustrates an example diagram and is not intended to be interpreted in a limiting manner, such as necessarily speci- fying the location, inclusion, and/or relative arrangement of the components described herein. For example, a data acqui- sition component 122 as illustrated in FIG. 1 can be part of a rotor 104 portion of an object examination apparatus 108, or more particularly can be part of a detector array 106, for example.

In the example environment 100, the object examination apparatus 108 is configured to examine one or more objects 102 (e.g., a series of suitcases at an airport, a human patient, etc.). The object examination apparatus 108 can comprise a rotor 104 and a stator 110. During an examination of the object(s) 102, the object(s) 102 can be placed on a support article 112, such as a bed or conveyor belt, that is selectively positioned in an examination region 114 (e.g., a hollow bore in the rotor 104 in which the object(s) 102 is exposed to radiation), and the rotor 104 can be rotated about the object(s) 102 by a rotator 116 (e.g., motor, drive shaft, chain, etc.).

The rotor 104 can surround a portion of the examination region 114 and can comprise one or more radiation sources 118 (e.g., an ionizing radiation source such as an x-ray source, gamma-ray source, etc.) and a detector array 106 that is mounted on a substantially diametrically opposite side of the rotor 104 relative to the radiation source(s) 118. During an examination of the object(s) 102, the radiation source(s) 118 emits fan and/or cone shaped radiation 120 configura- tions into the examination region 114 of the object examination apparatus 108. It may be appreciated that such radiation 120 can be emitted substantially continuously and/or can be emitted intermittently (e.g., a short pulse of radiation 120 is emitted followed by a resting period during which the radiation source(s) 118 is not activated).

As the emitted radiation 120 traverses the object(s) 102, the radiation 120 can be attenuated differently by different aspects of the object(s) 102. Because different aspects attenuate different percentages of the radiation 120, an image(s) can be generated based upon the attenuation, or variations in the number of radiation photons that are detected by the detector array 106. For example, more dense aspects of the object(s) 102, such as a bone or metal plate, can attenuate more of the radiation 120 (e.g., causing fewer photons to be detected by the detector array 106) than less dense aspects, such as skin or clothing.

The detector array 106 is configured to directly convert (e.g., using amorphous selenium and/or other direct conversion materials) and/or indirectly convert (e.g., using a scintillator and photodetectors and/or other indirect conversion materials) detected radiation into analog signals that can be transmitted from the detector array 106 to a data acquisition component 122 configured to convert the analog signals output by the detector array 106 into digital signals and/or to compile signals that were transmitted within a predetermined time interval, or measurement interval, using various techniques (e.g., integration, photon counting, etc.). It can be appreciated that such a measurement interval can be referred to as a "view" and generally reflects signals generated from radiation 120 that was emitted while the radiation source(s) 118 was at a particular angular range relative to the object 102. Based upon the compiled signals, the data acquisition component 122 can generate projection data indicative of the compiled signals, for example.

Information can be transmitted between components physically attached to the rotor 104 (e.g., such as the detector array 106 and/or data acquisition component 122) and components that are not physically attached to the rotor 104 (e.g., such as an image reconstructor 124) through a data communication system. By way of example, the projection space data (at times referred to as imaging data because it is used to reconstruct images of the object) generated by the data acquisition component 122 can be transmitted via the data communication system to an image reconstructor 124 positioned on the stator 110 of the imaging modality. As described in more detail below, such a data communication system typically comprises one or more data communication components mounted to the rotor 104 and to the stator 110, where an airgap generally separates a data communication component mounted to the rotor 104 from a data communication component mounted to the stator 110.

The image reconstructor 124 is configured to receive the projection space data that is output by the data acquisition component 122 and to generate image space data from the projection data using a suitable analytical, iterative, and/or other reconstruction technique (e.g., backprojection reconstruction, tomosynthesis reconstruction, iterative reconstruction, etc.). In this way, the data is converted from projection space to image space, a domain that may be more understandable by a user 130 viewing the image(s), for example.

The example environment 100 also comprises a terminal 126, or workstation (e.g., a computer), configured to receive the image(s), which can be displayed on a monitor 128 to the user 130 (e.g., security personnel, medical personnel, etc.). In this way, a user 130 can inspect the image(s) to identify areas of interest within the object(s) 102. The terminal 126 can also be configured to receive user input which can direct operations of the object examination apparatus 108 (e.g., a speed of a conveyor belt, activation of the radiation source (s) 118, etc.).

In the example environment 100, a controller 132 is operably coupled to the terminal 126. In one example, the controller 132 is configured to receive input from the terminal 126, such as user input for example, and to generate instructions for the object examination apparatus 108 indicative of operations to be performed. For example, the user 130 can desire to reexamine the object(s) 102 at a different energy level, and the controller 132 can issue a command instructing the support article 112 to reverse direction (e.g., bringing the object(s) 102 back into an examination region 114 of the object examination apparatus 108) and instructing a power supply mounted to the rotor 104 to increase a voltage applied to the radiation source(s) 118 (e.g., causing the radiation 120 output therefrom to have a higher energy).

Figure 2:
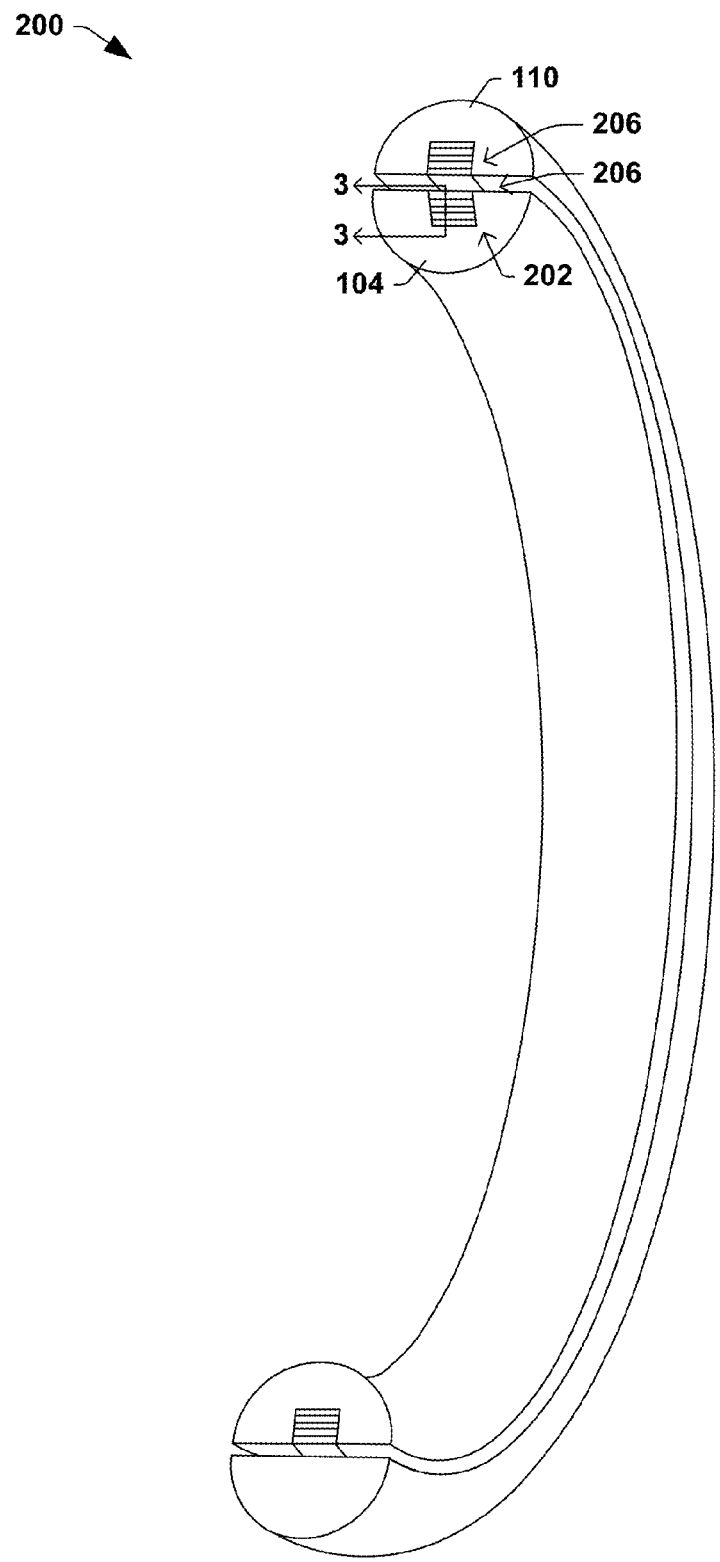
FIG. 2 illustrates an example rotor and stator, with a data communication system coupled to the rotor and the stator.

FIG. 2 illustrates a cross-sectional view of an example data communication system 200 (e.g., taken along line 2-2 in FIG. 1). The data communication system 200 comprises a first data communication component 202 that is mounted to a radial surface of the rotor 104. More particularly, the first data communication component 202 can be mounted to an exterior radial surface of the rotor 104. In another example, the first data communication component 202 may be mounted to an interior radial surface of the rotor 104 (e.g., where the interior radial surface defines an outer circumference of a bore into which the object 102 is inserted to be examined).

The rotor 104 is typically separated from the stator 110 by an airgap 204 that is defined by a space between the rotor 104 and the stator 110. The airgap 204 is configured to enable rotation of the rotor 104 relative to the stator 110. In an example, the first data communication component 202 can be mounted to the rotor 104 within and/or adjacent the airgap 204. In an example, a second data communication component 206 can be mounted on the stator 110 within and/or adjacent the airgap 204. The first data communication component 202 and the second data communication component 206 can form an electromagnetic coupling, such that data can be transmitted between (e.g., to and/or from) the first data communication component 202 and the second data communication component 206. Thus, the first data communication component 202 is configured to emit electromagnetic waves through the airgap 204 in the direction of the second data communication component 206, which is positioned on a diametrically opposite side of the airgap 204 relative to the first data communication component 202. The distance between the first data communication component 202 and the second data communication component 206 may be relatively small, given that the airgap 204 may typically be less than about 20 millimeters, although, in some examples, the airgap 204 may be more than about 20 millimeters.

In applications where the transmittal distance is relatively small, such as in radiation imaging modalities, typically at least one of the first data communication component 202 and the second data communication component 206 extend along substantially an entire surface of the rotor 104 and/or the stator 110 (e.g., forming a nearly complete ring). For example, in the illustrated example, the first data communication component 202 may extend along an outer circumference of the rotor 104 while the second data communication component 206 may be mounted to merely a small portion of an inner circumference of the stator 110. In this way, as the rotor 104, including the first data communication component 202, rotates, a portion of the first data communication component 202 remains in close spatial proximity to the second data communication component 206 (e.g., which may not form a complete ring along an inner surface of the stator 110).

It may be appreciated that where the first data communication component 202 forms a nearly complete ring around a bore of the radiation imaging modality through which an object is examined, the first data communication component 202, including a base plate, transmitting elements, and/or conducting portions of transmitting elements, may be said to be annular. Moreover, components of the first data communication component 202, such as the conducting portions of respective transmitting elements, that extend along the length of the first data communication component (e.g., where the length is measured as the circumference of the nearly complete ring) may be considered concentric because they share a common axis. This common axis may be parallel with an axis of rotation for the rotor 104, for example. It will be appreciated that in some examples, the first data communication component 202 is not limited to being mounted to the rotor 104 while the second data communication component 206 is not limited to being mounted to the stator 110. Rather, in another example, the first data communication component 202 may be mounted to the stator 110 while the second data communication component 206 may be mounted to the rotor 104.

Figure 3:
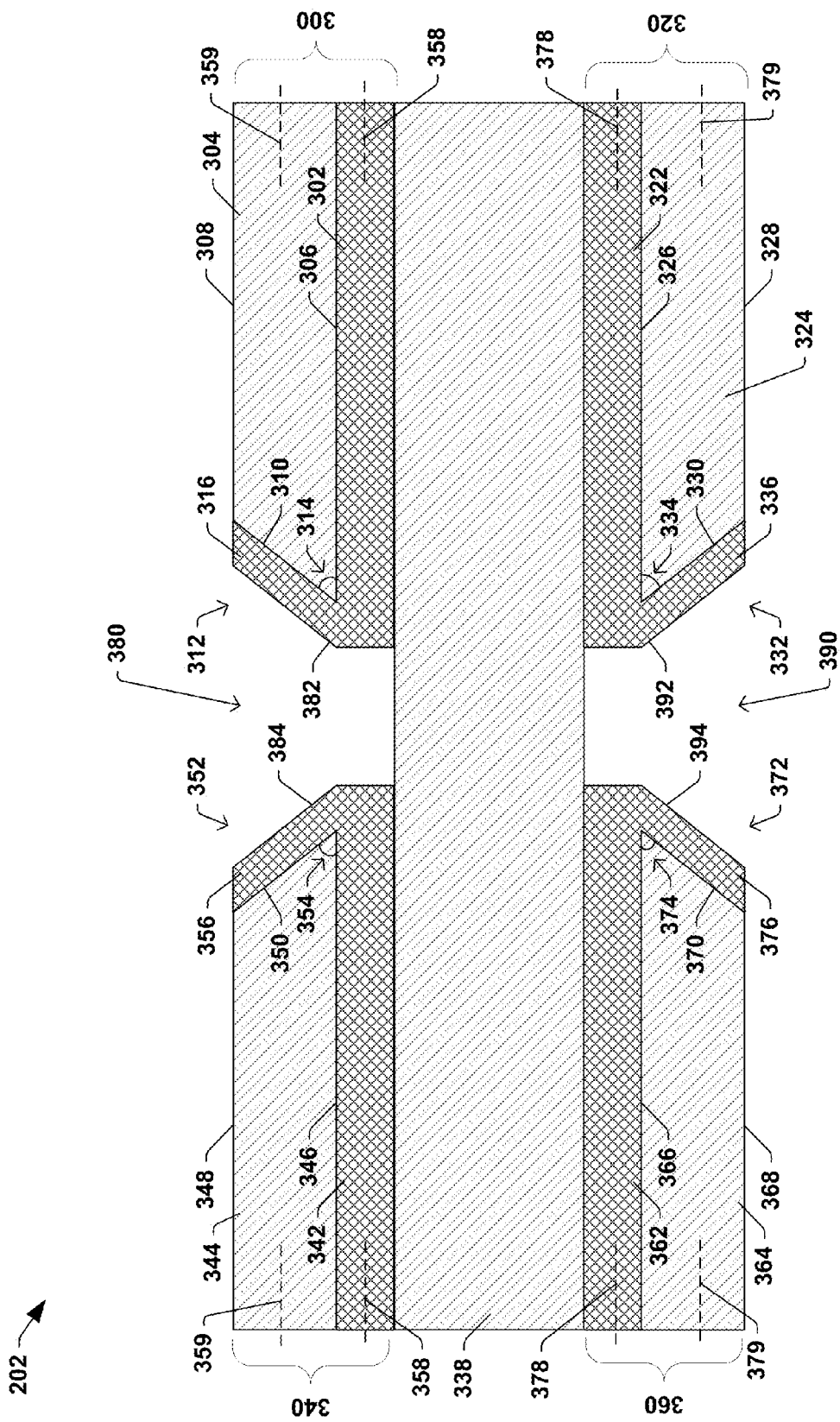
FIG. 3 illustrates a cross-sectional view of an example first data communication component.

FIG. 3 illustrates a cross-sectional view (e.g., taken along line 3-3 in FIG. 2) of an example of the first data communication component 202 of the data communication system 200. The first data communication component 202 can be mounted to the rotor 104 (e.g., as illustrated in FIG. 2) or the stator 110. As such, the first data communication component 202 can transmit data between the rotor 104 and the stator 110 or can receive data transmitted between the rotor 104 and the stator (e.g., by detecting electromagnetic waves). In an example, the first data communication component 202, when mounted to the stator 110 or the rotor 104, can extend circumferentially about an axis. While reference is made herein to the construction of the first data communication component 202 (e.g., extending circumferentially about the axis), the features describes herein may also be applicable to the second data communication component 206 (e.g., which may not extend circumferentially about the axis).

The first data communication component 202 comprises a first circuit board assembly 300. The first circuit board assembly 300 comprises a first conductive layer 302 and a first dielectric layer 304. In an example, the first conductive layer 302 comprises any number of materials that are electrically conductive and capable of transmitting electric current. In some examples, the first conductive layer 302 comprises conductive tracks, conductive traces, conductive ink, conductive pads, and/or conductive materials (e.g., copper, aluminum, etc.) that are attached to (e.g., mounted to, etc.) the first dielectric layer 304. In the illustrated example, the first conductive layer 302 is disposed on one side of the first dielectric layer 304, though, in other examples, a plurality of conductive layers may be provided, such as on opposing sides of the first dielectric layer 304.

The first dielectric layer 304 may be disposed radially outwardly from the first conductive layer 302. That is, when the first data communication component 202 extends circumferentially about an axis (e.g., as illustrated in FIG. 2), the first dielectric layer 304 may be located a farther radial distance from the axis than the first conductive layer 302. In an example, the first dielectric layer 304 comprises any number of materials that are electrically insulating and are resistant to the flow of electric current through the first dielectric layer 304. In some examples, the first dielectric layer 304 comprises a substrate onto which the first conductive layer 302 is applied. The first dielectric layer 304 can comprise, for example, one or more of fiberglass, silicon, silicon dioxide, aluminum oxide, sapphire, germanium, gallium arsenide, etc.

The first dielectric layer 304 has a first surface 306 and a second surface 308. In an example, the first surface 306 is located at an inner radial location of the first dielectric layer 304, while the second surface 308 is located at an outer radial location of the first dielectric layer 304. In this example, the first surface 306 is in contact with the first conductive layer 302. That is, the first surface 306 can face the first conductive layer 302, with the first conductive layer 302 attached to, formed on, etc. the first surface 306 of the first dielectric layer 304. The second surface 308 can face away from the first conductive layer 302, such that the second surface 308 may not be in contact with the first conductive layer 302. In this example, the second surface 308 is substantially parallel to the first surface 306.

The first dielectric layer 304 has a first lateral surface 310 that defines a first end 312 of the first dielectric layer 304. In this example, the first lateral surface 310 extends between the first surface 306 and the second surface 308. The first lateral surface 310 can extend non-parallel to the first surface 306 and/or the second surface 308. In this example, the first lateral surface 310 can define a first angle 314 with respect to the first surface 306. While the first angle 314 in this example is illustrated as being less than about 90 degrees, a variety of ranges for the first angle 314 are envisioned. For example, the first angle 314 can be between about 15 degrees to about 75 degrees. In other examples, the first angle 314 can be between about 45 degrees to about 135 degrees. Indeed, the first angle 314 can comprise nearly any magnitude between about 0 degrees to about 180 degrees.

The first conductive layer 302 can comprise a first conductive edge 316 that extends from the first surface 306 of the first dielectric layer 304 towards the second surface 308 of the first dielectric layer 304. In this example, the first conductive edge 316 can extend along the first lateral surface 310. For example, the first conductive edge 316 can be in contact with and/or extend adjacent to the first lateral surface 310.

The first data communication component 202 comprises a second circuit board assembly 320. The second circuit board assembly 320 comprises a second conductive layer 322 and a second dielectric layer 324. In an example, the second conductive layer 322 comprises any number of materials that are electrically conductive and capable of transmitting electric current. In some examples, the second conductive layer 322 comprises conductive tracks, conductive traces, conductive ink, conductive pads, and/or conductive materials (e.g., copper, etc.) that are attached to (e.g., mounted to, etc.) the second dielectric layer 324. In the illustrated example, the second conductive layer 322 is disposed on one side of the second dielectric layer 324, though, in other examples, a plurality of conductive layers may be provided, such as on opposing sides of the second dielectric layer 324.

The second circuit board assembly 320 can be spaced apart from the first circuit board assembly 300. In this example, the second circuit board assembly 320 can be disposed radially inwardly from the first circuit board assembly 300. As such, the second circuit board assembly 320 can be located closer to the axis about which the first data communication component 202 circumferentially extends.

The second dielectric layer 324 may be disposed radially inwardly from the second conductive layer 322. That is, when the first data communication component 202 extends circumferentially about the axis (e.g., as illustrated in FIG. 2), the second dielectric layer 324 may be located a closer radial distance from the axis than the second conductive layer 322. In an example, the second dielectric layer 324 comprises any number of materials that are electrically insulating and are resistant to the flow of electric current through the second dielectric layer 324. In some examples, the second dielectric layer 324 comprises a substrate onto which the second conductive layer 322 is applied. The second dielectric layer 324 can comprise, for example, one or more of fiberglass, silicon, silicon dioxide, aluminum oxide, sapphire, germanium, gallium arsenide, etc.

The second dielectric layer 324 has a third surface 326 and a fourth surface 328. In an example, the third surface 326 is located at an outer radial location of the second dielectric layer 324, while the fourth surface 328 is located at an inner radial location of the second dielectric layer 324. In this example, the third surface 326 is in contact with the second conductive layer 322. That is, the third surface 326 can face the second conductive layer 322, with the second conductive layer 322 attached to, formed on, etc. the third surface 326 of the second dielectric layer 324. The fourth surface 328 can face away from the second conductive layer 322, such that the fourth surface 328 may not be in contact with the second conductive layer 322. In this example, the fourth surface 328 is substantially parallel to the third surface 326.

The second dielectric layer 324 has a second lateral surface 330 that defines a first end 332 of the second dielectric layer 324. In this example, the second lateral surface 330 extends between the third surface 326 and the fourth surface 328. The second lateral surface 330 can extend non-parallel to the third surface 326 and/or the fourth surface 328. In this example, the second lateral surface 330 can define a second angle 334 with respect to the third surface 326. While the second angle 334 in this example is illustrated as being less than about 90 degrees, a variety of ranges for the second angle 334 are envisioned. For example, the second angle 334 can be between about 15 degrees to about 75 degrees. In other examples, the second angle 334 can be between about 45 degrees to about 135 degrees. Indeed, the second angle 334 can comprise nearly any magnitude between about 0 degrees to about 180 degrees.

The second conductive layer 322 can comprise a second conductive edge 336 that extends from the third surface 326 of the second dielectric layer 324 towards the fourth surface 328 of the second dielectric layer 324. In this example, the second conductive edge 336 can extend along the second lateral surface 330. For example, the second conductive edge 336 can be in contact with and/or extend adjacent to the second lateral surface 330.

The first data communication component 202 comprises an insulating layer 338 that is disposed between the first conductive layer 302 of the first circuit board assembly 300 and the second conductive layer 322 of the second circuit board assembly 320. In this example, the insulating layer 338 comprises any number of materials that are electrically insulating and are resistant to the flow of electric current through the insulating layer 338. As such, electric current flow between the first conductive layer 302 and the second conductive layer 322 through the insulating layer 338 is substantially limited. In some examples, the insulating layer 338 can comprise one or more of polystyrene, fiberglass, silicon, silicon dioxide, aluminum oxide, sapphire, germanium, gallium arsenide, etc.

In this example, the first data communication component 202 comprises a third circuit board assembly 340. The third circuit board assembly 340 comprises a third conductive layer 342 and a third dielectric layer 344. In an example, the third conductive layer 342 may be similar in some respects to the first conductive layer 302 and/or the second conductive layer 322. For example, the third conductive layer 342 may comprise any number of materials that are electrically conductive and capable of transmitting electric current. For example, the third conductive layer 342 may comprise conductive tracks, conductive traces, conductive ink, conductive pads, and/or conductive materials (e.g., copper, etc.) that are attached to (e.g., mounted to, etc.) the third dielectric layer 344.

The third dielectric layer 344 may be disposed radially outwardly from the third conductive layer 342. The third dielectric layer 344 may be similar in some respects to the first dielectric layer 304 and/or the second dielectric layer 324. For example, the third dielectric layer 344 may comprise materials that are electrically insulating and are resistant to the flow of electric current through the third dielectric layer 344. For example, the third dielectric layer 344 may comprise a substrate onto which the third conductive layer 342 is applied. The third dielectric layer 344 can comprise, for example, one or more of fiberglass, silicon, silicon dioxide, aluminum oxide, sapphire, germanium, gallium arsenide, etc.

The third dielectric layer 344 has a first surface 346 and a second surface 348. In an example, the first surface 346 is located at an inner radial location of the third dielectric layer 344, while the second surface 348 is located at an outer radial location of the third dielectric layer 344. In this example, the first surface 346 is in contact with the third conductive layer 342. That is, the first surface 346 can face the third conductive layer 342, with the third conductive layer 342 attached to, formed on, etc. the first surface 346 of the third dielectric layer 344. The second surface 348 can face away from the third conductive layer 342, such that the second surface 348 may not be in contact with the third conductive layer 342. In this example, the second surface 348 is substantially parallel to the first surface 306.

The third dielectric layer 344 has a third lateral surface 350 that defines a second end 352 of the third dielectric layer 344. In this example, the third lateral surface 350 extends between the first surface 346 and the second surface 348. The third lateral surface 350 can extend non-parallel to the first surface 346 and/or the second surface 348. In this example, the third lateral surface 350 can define a third angle 354 with respect to the first surface 346. While the third angle 354 in this example is illustrated as being less than about 90 degrees, a variety of ranges for the third angle 354 are envisioned. For example, the third angle 354 can be between about 15 degrees to about 75 degrees. In other examples, the third angle 354 can be between about 45 degrees to about 135 degrees. Indeed, the third angle 354 can comprise nearly any magnitude between about 0 degrees to about 180 degrees.

The third conductive layer 342 can comprise a third conductive edge 356 that extends from the first surface 346 of the third dielectric layer 344 towards the second surface 348 of the third dielectric layer 344. In this example, the third conductive edge 356 can extend along the third lateral surface 350. For example, the third conductive edge 356 can be in contact with and/or extend adjacent to the third lateral surface 350.

The third circuit board assembly 340 can be circumferentially aligned with the first circuit board assembly 300. That is, by being circumferentially aligned, the first circuit board assembly 300 and the third circuit board assembly 340 can be located substantially the same distance from the axis about which the first data communication component 202 circumferentially extends. In this example, the third circuit board assembly 340 and the first circuit board assembly 300 can extend substantially parallel to each other. In this example, the third circuit board assembly 340 and the first circuit board assembly 300 can extend substantially coaxial with respect to each other.

The third conductive layer 342 can be circumferentially aligned with the first conductive layer 302 of the first circuit board assembly 300. That is, by being circumferentially aligned, the first conductive layer 302 and the third conductive layer 342 can be located substantially the same distance from the axis about which the first data communication component 202 circumferentially extends. In this example, the first conductive layer 302 and the third conductive layer 342 can extend along a first axis 358. It will be appreciated that while the first axis 358 appears to be substantially straight in FIG. 3, the first axis 358 may instead have a substantially circular shape due to the first data communication component 202 circumferentially extending around the axis.

The third dielectric layer 344 can be circumferentially aligned with the first dielectric layer 304 of the first circuit board assembly 300. That is, by being circumferentially aligned, the first dielectric layer 304 and the third dielectric layer 344 can be located substantially the same distance from the axis about which the first data communication component 202 circumferentially extends. In this example, the first dielectric layer 304 and the third dielectric layer 344 can extend along a second axis 359. It will be appreciated that while the second axis 359 appears to be substantially straight in FIG. 3, the second axis 359 may instead have a substantially circular shape.

The first data communication component 202 comprises a fourth circuit board assembly 360. The fourth circuit board assembly 360 comprises a fourth conductive layer 362 and a fourth dielectric layer 364. In an example, the fourth conductive layer 362 may be similar in some respects to the first conductive layer 302, the second conductive layer 322, and/or the third conductive layer 342. For example, the fourth conductive layer 362 may comprise conductive tracks, conductive traces, conductive ink, conductive pads, and/or conductive materials (e.g., copper, etc.) that are attached to (e.g., mounted to, etc.) the fourth dielectric layer 364.

The fourth circuit board assembly 360 can be spaced apart from the third circuit board assembly 340. In this example, the fourth circuit board assembly 360 can be disposed radially inwardly from the third circuit board assembly 340. As such, the fourth circuit board assembly 360 can be located closer to the axis about which the first data communication component 202 circumferentially extends.

The fourth dielectric layer 364 may be disposed radially inwardly from the fourth conductive layer 362. The fourth dielectric layer 364 may be similar in some respects to the first dielectric layer 304, the second dielectric layer 324, and/or the third dielectric layer 344. For example, the fourth dielectric layer 364 may comprise materials that are electrically insulating and are resistant to the flow of electric current through the fourth dielectric layer 364. For example, the fourth dielectric layer 364 may comprise a substrate onto which the fourth conductive layer 362 is applied. The fourth dielectric layer 364 can comprise, for example, one or more of fiberglass, silicon, silicon dioxide, aluminum oxide, sapphire, germanium, gallium arsenide, etc.

The fourth dielectric layer 364 has a third surface 366 and a fourth surface 368. In an example, the third surface 366 is located at an outer radial location of the fourth dielectric layer 364, while the fourth surface 368 is located at an inner radial location of the fourth dielectric layer 364. In this example, the third surface 366 is in contact with the fourth conductive layer 362. That is, the third surface 366 can face the fourth conductive layer 362, with the fourth conductive layer 362 attached to, formed on, etc. the third surface 366 of the fourth dielectric layer 364. The fourth surface 368 can face away from the fourth conductive layer 362. In this example, the fourth surface 368 is substantially parallel to the third surface 366.

The fourth dielectric layer 364 has a fourth lateral surface 370 that defines a second end 372 of the fourth dielectric layer 364. In this example, the fourth lateral surface 370 extends between the third surface 366 and the fourth surface 368. The fourth lateral surface 370 extends non-parallel to the third surface 366 and/or the fourth surface 368. In this example, the fourth lateral surface 370 can define a fourth angle 374 with respect to the third surface 366. While the fourth angle 374 in this example is illustrated as being less than about 90 degrees, a variety of ranges of the fourth angle 374 are envisioned. For example, the fourth angle 374 can be between about 15 degrees to about 75 degrees. In other examples, the fourth angle 374 can be between about 45 degrees to about 135 degrees. Indeed, the fourth angle 374 can comprise nearly any magnitude between about 0 degrees to about 180 degrees.

The fourth conductive layer 362 can comprise a fourth conductive edge 376 that extends from the third surface 366 of the fourth dielectric layer 364 towards the fourth surface 368 of the fourth dielectric layer 364. In this example, the fourth conductive edge 376 can extend along the fourth lateral surface 370. For example, the fourth conductive edge 376 can be in contact with and/or extend adjacent to the fourth lateral surface 370.

The fourth circuit board assembly 360 can be circumferentially aligned with the second circuit board assembly 320. That is, by being circumferentially aligned, the second circuit board assembly 320 and the fourth circuit board assembly 360 can be located substantially the same distance from the axis about which the first data communication component 202 circumferentially extends. In this example, the fourth circuit board assembly 360 and the second circuit board assembly 320 can extend substantially parallel to each other. In this example, the fourth circuit board assembly 360 and the second circuit board assembly 320 can extend substantially coaxial with respect to each other.

The fourth conductive layer 362 can be circumferentially aligned with the second conductive layer 322 of the second circuit board assembly 320. That is, by being circumferentially aligned, the second conductive layer 322 and the fourth conductive layer 362 can be located substantially the same distance from the axis about which the first data communication component 202 circumferentially extends. In this example, the second conductive layer 322 and the fourth conductive layer 362 can extend along a third axis 378. It will be appreciated that while the third axis 378 appears to be substantially straight in FIG. 3, the third axis 378 may instead have a substantially circular shape due to the first data communication component 202 circumferentially extending around the axis.

The fourth dielectric layer 364 can be circumferentially aligned with the second dielectric layer 324 of the second circuit board assembly 320. That is, by being circumferentially aligned, the second dielectric layer 324 and the fourth dielectric layer 364 can be located substantially the same distance from the axis about which the first data communication component 202 circumferentially extends. In this example, the second dielectric layer 324 and the fourth dielectric layer 364 can extend along a fourth axis 379. It will be appreciated that while the fourth axis 379 appears to be substantially straight in FIG. 3, the fourth axis 379 may instead have a substantially circular shape.

The insulating layer 338 can extend between the third circuit board assembly 340 and the fourth circuit board assembly 360. In an example, the insulating layer 338 extends between the third conductive layer 342 of the third circuit board assembly 340 and the fourth conductive layer 362 of the fourth circuit board assembly 360. In this example, the insulating layer 338 can limit electric current flow between the first conductive layer 302 and the second conductive layer 322 and between the third conductive layer 342 and the fourth conductive layer 362. In this example, the insulating layer 338 can extend substantially continuously between the circuit board assemblies 300, 320, 340, 360. In still other embodiments, a second insulating layer (not shown) may instead extend between the third circuit board assembly 340 and the fourth circuit board assembly 360.

The first circuit board assembly 300 can be circumferentially spaced apart (e.g., along the first axis 358 and the second axis 359) from the third circuit board assembly 340 to define a first retainer opening 380 between the first circuit board assembly 300 and the third circuit board assembly 340. The first retainer opening 380 may be bounded on opposing sides by the first conductive edge 316 of the first conductive layer 302, by the third conductive edge 356 of the third conductive layer 342, and by the insulating layer 338. That is, the first conductive edge 316 of the first conductive layer 302 can define a first side 382 of the first retainer opening 380. The third conductive edge 356 of the third conductive layer 342 can define a second side 384 of the first retainer opening 380. In this example, the first retainer opening 380 can have a non-constant size. For example, in a direction away from the insulating layer 338 (e.g., upwardly towards a top of the page in FIG. 3), the first retainer opening 380 can have an increasing size.

The second circuit board assembly 320 can be circumferentially spaced apart (e.g., along the third axis 378 and the fourth axis 379) from the fourth circuit board assembly 360 to define a second retainer opening 390 between the second circuit board assembly 320 and the fourth circuit board assembly 360. The second retainer opening 390 may be bounded on opposing sides by the second conductive edge 336 of the second conductive layer 322, by the fourth conductive edge 376 of the fourth conductive layer 362, and by the insulating layer 338. That is, the second conductive edge 336 of the second conductive layer 322 can define a first side 392 of the second retainer opening 390. The fourth conductive edge 376 of the fourth conductive layer 362 can define a second side 394 of the second retainer opening 390. In this example, the second retainer opening 390 can have a non-constant size. For example, in a direction away from the insulating layer 338 (e.g., downwardly towards a bottom of the page in FIG. 3), the second retainer opening 390 can have an increasing size.

Figure 4:
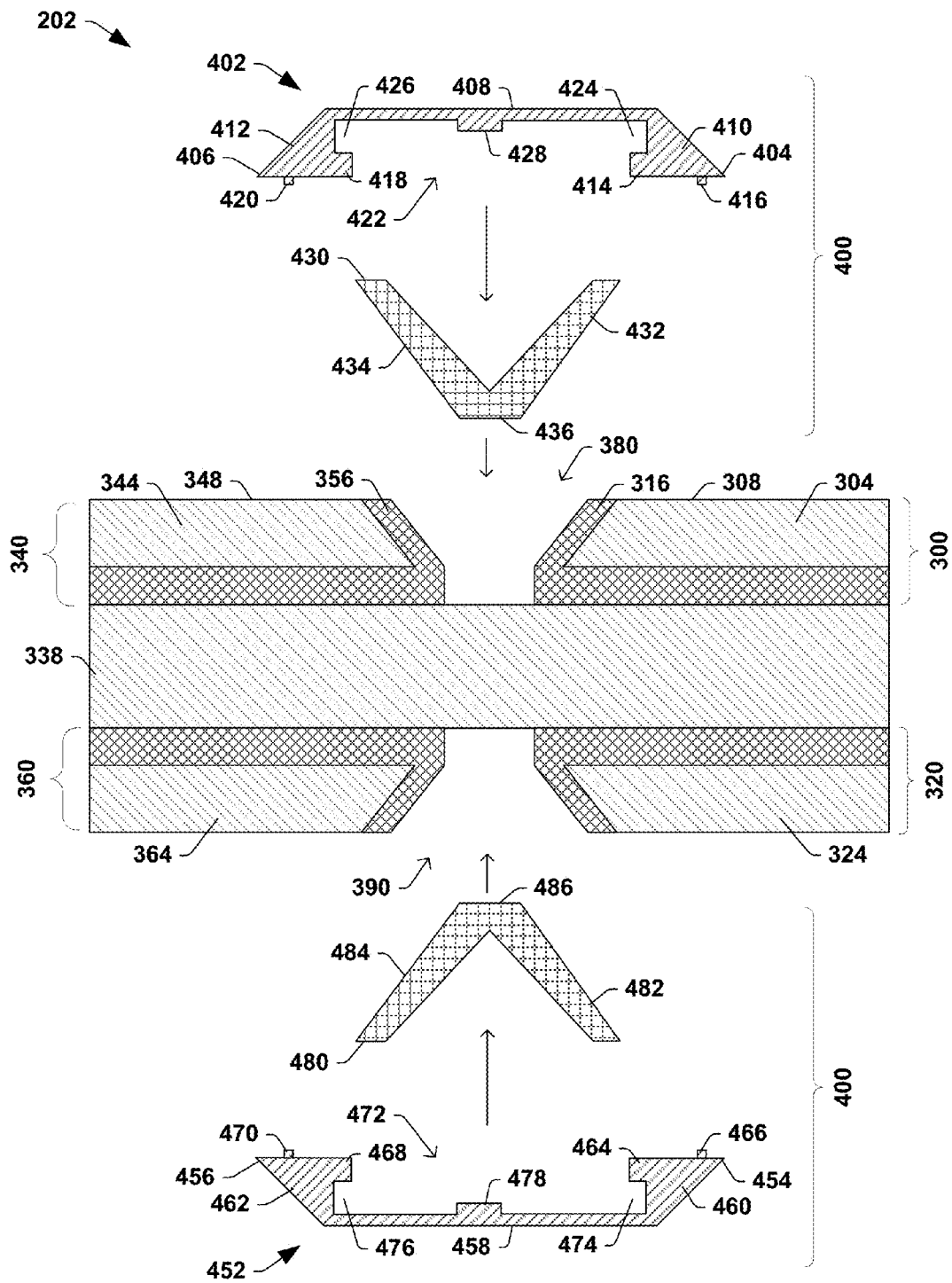
FIG. 4 illustrates an example first data communication component having an example support structure.
Figure 5:
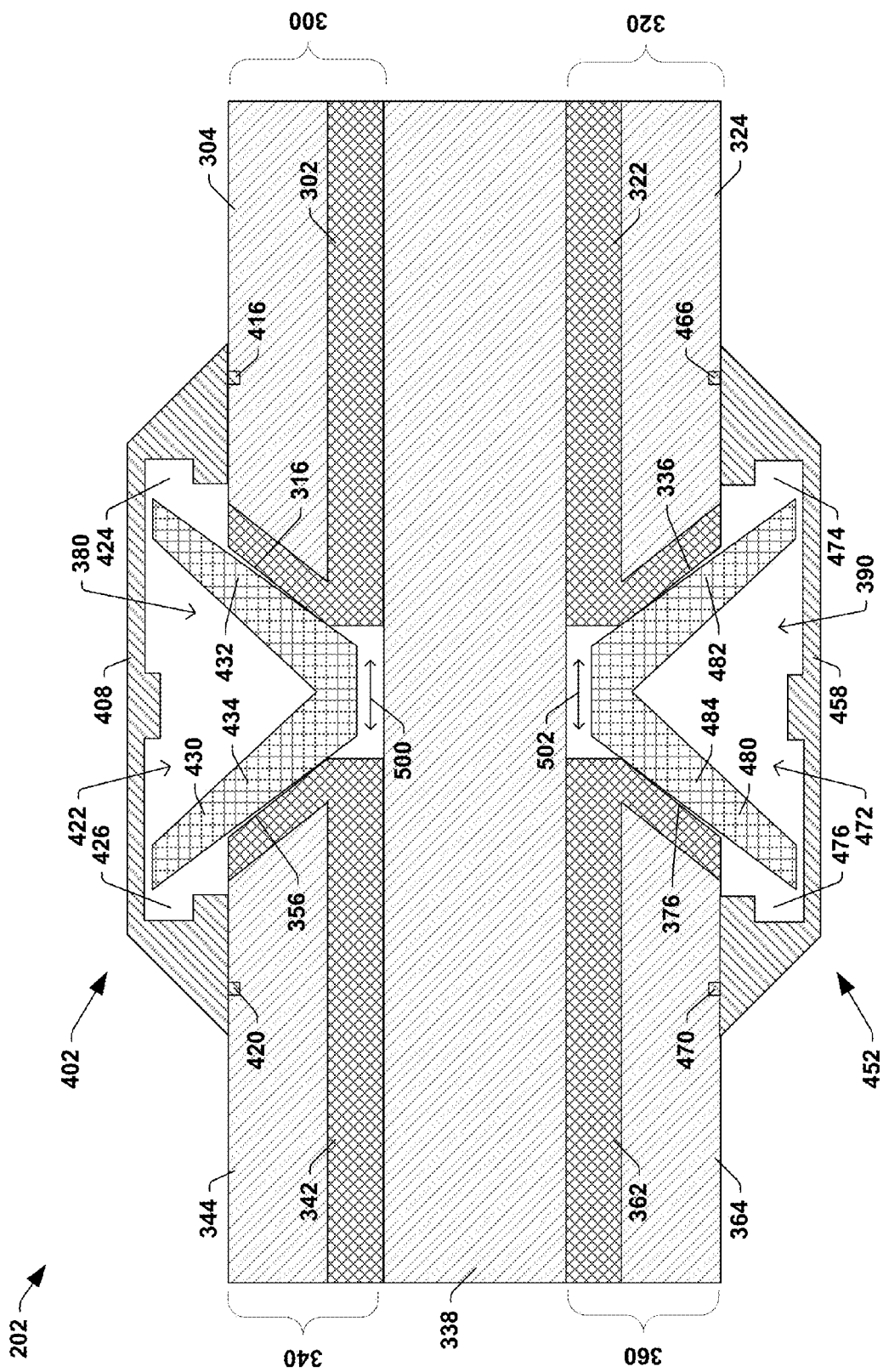
FIG. 5 illustrates an example first data communication component in association with an example support structure.

Referring to FIG. 4, the first data communication component 202 comprises a support structure 400. The support structure 400 can circumferentially surround one or more of the first circuit board assembly 300, the second circuit board assembly 320, the third circuit board assembly 340, the fourth circuit board assembly 360, and/or the insulating layer 338. As such, the support structure 400 can maintain a relative position of the first circuit board assembly 300, the second circuit board assembly 320, the third circuit board assembly 340, the fourth circuit board assembly 360, and/or the insulating layer 338. It is to be appreciated that the support structure 400 is illustrated as being partially exploded in FIG. 4 for the purposes of illustration and to more clearly show portions of the support structure 400. In another example, however, as illustrated in FIG. 5, the support structure 400 can be in contact with and/or in proximity to one or more of the circuit board assemblies.

The support structure 400 comprises a first attachment housing 402. The first attachment housing 402 is configured to attach the first circuit board assembly 300 to the third circuit board assembly 340. In this example, the first attachment housing 402 extends between a first end 404 and a second end 406. The first end 404 can be in proximity to and/or radially intersecting (e.g., by being located along a radial path from the axis, through the first circuit board assembly 300, and through the first end 404 of the first attachment housing 402) the first circuit board assembly 300. The second end 406 can be in proximity to and/or radially intersecting (e.g., by being located along a radial path from the axis, through the third circuit board assembly 340, and through the second end 406 of the first attachment housing 402) the third circuit board assembly 340. In an example, the first attachment housing 402 has a length (e.g., as defined between the first end 404 and the second end 406) that is greater than or equal to a maximum distance that separates the first conductive edge 316 and the third conductive edge 356.

The first attachment housing 402 comprises a first body portion 408 that extends between the first end 404 and the second end 406. The first body portion 408 comprises any number of materials, such as plastics, metals, non-conductive materials, or the like. The first body portion 408 has at least some degree of stiffness and/or rigidity, such that the first body portion 408 is relatively resistant to inadvertent bending, flexing, torsion, fracture, or the like. As such, the first body portion 408 can substantially maintain the relative positions of the first circuit board assembly 300 and the third circuit board assembly 340.

The first attachment housing 402 comprises a first leg 410 and a second leg 412. The first leg 410 can be attached to the first body portion 408 at the first end 404. The second leg 412 can be attached to the first body portion 408 at the second end 406. In this example, the first leg 410 can project from the first body portion 408 towards the first circuit board assembly 300. The second leg 412 can project from the first body portion 408 towards the third circuit board assembly 340. In this example, the first leg 410 and/or the second leg 412 can have a substantially triangular shape, though, any number of shapes are envisioned. The first leg 410 and/or the second leg 412 can comprise a substantially similar material as the first body portion 408. In an example, the first leg 410 is configured to be attached to the first circuit board assembly 300. In an example, the second leg 412 is configured to be attached to the third circuit board assembly 340.

The first leg 410 comprises a first base portion 414. The first base portion 414 is located at an end of the first leg 410 that is opposite the first body portion 408. In this example, the first base portion 414 can be in proximity to and/or in contact with an outer radial surface (e.g., the second surface 308) of the first circuit board assembly 300. The first base portion 414 can have a larger cross-sectional size (e.g., as measured left and right in FIG. 4) than other portions of the first leg 410.

In an example, the first base portion 414 comprises a first attachment structure 416. The first attachment structure 416 can extend from a lower surface of the first base portion 414 towards the first circuit board assembly 300. The first attachment structure 416 can comprise, for example, a protrusion, an extension, a protuberance, an adhesive, a mechanical fastener (e.g., screws, bolts, etc.), etc. Indeed, the first attachment structure 416 comprises any number of structures that can function to attach the first end 404 of the first attachment housing 402 to the first dielectric layer 304 of the first circuit board assembly 300.

The second leg 412 comprises a second base portion 418. The second base portion 418 is located at an end of the second leg 412 that is opposite the first body portion 408. In this example, the second base portion 418 can be in proximity to and/or in contact with an outer radial surface (e.g., the second surface 348) of the third circuit board assembly 340. The second base portion 418 can have a larger cross-sectional size (e.g., as measured left and right in FIG. 4) than other portions of the second leg 412.

In an example, the second base portion 418 comprises a second attachment structure 420. The second attachment structure 420 can extend from a lower surface of the second base portion 418 towards the third circuit board assembly 340. The second attachment structure 420 can comprise, for example, a protrusion, an extension, a protuberance, an adhesive, a mechanical fastener (e.g., screws, bolts, etc.), etc. Indeed, the second attachment structure 420 comprises any number of structures that can function to attach the second end 406 of the first attachment housing 402 to the third dielectric layer 344 of the third circuit board assembly 340.

A first opening 422 is defined within the first attachment housing 402. In this example, the first opening 422 is defined between the first body portion 408, the first leg 410, and the second leg 412. In this example, the first opening 422 is elongated and has a length (e.g., measured left-to-right on the page) that is greater than a height (e.g., measured top-to-bottom on the page). The first opening 422 has a first channel 424 and a second channel 426 located at opposing ends of the first opening 422. In this example, the first channel 424 is defined between the first body portion 408 and the first base portion 414 of the first leg 410. The second channel 426 is defined between the first body portion 408 and the second base portion 418 of the second leg 412. In an example, the first body portion 408 comprises a first projection 428 that projects from an inner surface of the first body portion 408 towards the insulating layer 338.

The first attachment housing 402 comprises a first conductive retainer 430. The first conductive retainer 430 can be disposed at least partially within the first retainer opening 380 and/or the first opening 422. The first conductive retainer 430 can be in proximity to and/or in contact with the first conductive edge 316 and the third conductive edge 356. The first conductive retainer 430 comprises any number of electrically conductive materials that are capable of transmitting electric current, such as metal materials (e.g., copper, etc.). In some examples, the first conductive retainer 430 comprises an electrically conductive spring mechanism, conductive solder, conductive epoxy, conductive paste, conductive glue, conductive fasteners, etc.

In the illustrated example, the first conductive retainer 430 comprises a first conductive portion 432 and a second conductive portion 434. The first conductive portion 432 and the second conductive portion 434 may be joined together at a central portion 436 (e.g., which may also be conductive). Together, the first conductive portion 432, the second conductive portion 434, and the central portion 436 can form a substantially V-shaped structure. In this example, the first conductive portion 432 extends from the central portion 436 at an angle that is between about 15 degrees to about 75 degrees. In this example, the second conductive portion 434 extends from the central portion 436 at an angle that is between about 15 degrees to about 75 degrees. In some examples, the first conductive portion 432 and/or the second conductive portion 434 have at least some degree of pliability and/or flexibility, such that the first conductive portion 432 and/or the second conductive portion 434 can flex towards each other, away from each other, etc.

The support structure 400 comprises a second attachment housing 452. The second attachment housing 452 is configured to attach the second circuit board assembly 320 to the fourth circuit board assembly 360. In this example, the second attachment housing 452 extends between a first end 454 and a second end 456. The first end 454 can be in proximity to and/or radially intersecting (e.g., by being located along a radial path from the axis, through the second circuit board assembly 320, and through the first end 454 of the second attachment housing 452) the second circuit board assembly 320. The second end 456 can be in proximity to and/or radially intersecting (e.g., by being located along a radial path from the axis, through the fourth circuit board assembly 360, and through the second end 456 of the second attachment housing 452) the fourth circuit board assembly 360.

The second attachment housing 452 is similar in some respects to the first attachment housing 402. For example, the second attachment housing 452 comprises a second body portion 458 that is similar to the first body portion 408. The second body portion 458 extends between the first end 454 and the second end 456. The second body portion 458 comprises a first leg 460 and a second leg 462, which are similar to the first leg 410 and the second leg 412 of the first body portion 408. The first leg 460 comprises the first base portion 464 while the second leg 462 comprises the second base portion 468. The first base portion 464 has a first attachment structure 466 while the second base portion 468 has a second attachment structure 470. The first attachment structure 466 can function to attach the first end 454 of the second attachment housing 452 to the second dielectric layer 324 of the second circuit board assembly 320. The second attachment structure 470 can function to attach the second end 466 of the second attachment housing 452 to the fourth dielectric layer 364 of the fourth circuit board assembly 360.

A second opening 472 is defined within the second attachment housing 452. In this example, the second opening 472 is defined between the second body portion 458, the first leg 460, and the second leg 462. The second opening 472 has a first channel 474 and a second channel 476 located at opposing ends of the first opening 422. The first channel 474 is defined between the second body portion 458 and the first base portion 464 of the first leg 460. The second channel 476 is defined between the second body portion 458 and the second base portion 468 of the second leg 462. In an example, the second body portion 458 comprises a second projection 478 that projects from an inner surface of the second body portion 458 towards the insulating layer 338.

The second attachment housing 452 comprises a second conductive retainer 480. The second conductive retainer 480 can be disposed at least partially within the second retainer opening 390 and/or the second opening 472. The second conductive retainer 480 is similar in structure to the first conductive retainer 430. For example, the second conductive retainer 480 comprises a first conductive portion 482 and a second conductive portion 484 that are joined together at a central portion 486 (e.g., which may also be conductive).

Turning to FIG. 5, the support structure 400 is illustrated in attachment with the first circuit board assembly 300, the second circuit board assembly 320, the third circuit board assembly 340, and the fourth circuit board assembly 360. In this example, the first conductive retainer 430 can be positioned at least partially within the first retainer opening 380 that is defined between the first circuit board assembly 300 and the third circuit board assembly 340. In an example, the first conductive portion 432 of the first conductive retainer 430 can be in contact with the first conductive edge 316 of the first conductive layer 302. In an example, the second conductive portion 434 of the first conductive retainer 430 can be in contact with the third conductive edge 356 of the third conductive layer 342. As such, in this example, the first conductive retainer 430 can be electrically coupled to the first conductive edge 316 of the first conductive layer 302 and the third conductive edge 356 of the third conductive layer 342. In such an example, the first conductive layer 302 can be electrically coupled to the third conductive layer 342, such that electric current can flow (e.g., flow illustrated with arrowhead 500) between the first conductive layer 302 and the third conductive layer 342. In some examples, electrical signals (e.g., related to imaging data, status information, etc.) can be transmitted through the first conductive layer 302 and/or the third conductive layer 342. In other examples, the second conductive layer 322 and/or the fourth conductive layer 362 may be coupled to a voltage source (e.g., ground) configured to maintain a substantially constant voltage on the second conductive layer 322 and/or the fourth conductive layer 362.

Portions of the first conductive retainer 430 can extend into the first opening 422 of the first attachment housing 402. For example, upper portions of the first conductive portion 432 and/or the second conductive portion 434 can be positioned to extend into the first opening 422 of the first attachment housing 402. In some examples, the first conductive portion 432 and/or the second conductive portion 434 can contact the first body portion 408, with the first body portion 408 applying a downward force to the first conductive portion 432 and/or the second conductive portion 434. In response to this force, the first conductive portion 432 and/or the second conductive portion 434 can flex outwardly. This outward flexion can cause upper portions of the first conductive portion 432 and/or the second conductive portion 434 to extend into the first channel 424 and/or the second channel 426. Additionally, the first body portion 408 can function to maintain the first conductive retainer 430 within the first retainer opening 380, thus ensuring that the first conductive retainer 430 remains in contact with the first conductive layer 302 and the third conductive layer 342.

To assist in attaching the first circuit board assembly 300 with respect to the third circuit board assembly 340, the first attachment structure 416 and the second attachment structure 420 can be attached to the first circuit board assembly 300 and the third circuit board assembly 340, respectively. For example, the first attachment structure 416 of the first attachment housing 402 can be attached to the first dielectric layer 304 of the first circuit board assembly 300. In this example, the first attachment structure 416 is illustrated as being at least partially embedded into the first dielectric layer 304. Similarly, in this example, the second attachment structure 420 can be attached to the third dielectric layer 344 of the third circuit board assembly 340, such as by being at least partially embedded into the third dielectric layer 344.

It will be appreciated that other methods of attachment are envisioned for attaching the first attachment housing 402 to the first circuit board assembly 300 and the third circuit board assembly 340. For example, the first attachment structure 416 and/or the second attachment structure 420 may comprise an adhesive (e.g., an epoxy, glue, etc.), such that the first attachment structure 416 can adhere to the first dielectric layer 304 while the second attachment structure 420 can adhere to the third dielectric layer 344. In another example, the first attachment structure 416 and/or the second attachment structure 420 can comprise fasteners (e.g., screws, bolts, clamps, etc.), such that the first attachment housing 402 can be attached (e.g., by threading attachment) to the first circuit board assembly 300 and the third circuit board assembly 340. In these examples, the first attachment housing 402 can function to attach the first circuit board assembly 300 and the third circuit board assembly 340, such that inadvertent movement and/or separation is substantially limited (e.g., mitigated).

In this example, the second conductive retainer 480 can be positioned at least partially within the second retainer opening 390 that is defined between the second circuit board assembly 320 and the fourth circuit board assembly 360. The first conductive portion 482 of the second conductive retainer 480 can be in contact with the second conductive edge 336 of the second conductive layer 322. In an example, the second conductive portion 484 of the second conductive retainer 480 can be in contact with the fourth conductive edge 376 of the fourth conductive layer 362. As such, in this example, the second conductive retainer 480 can be electrically coupled to the second conductive edge 336 of the second conductive layer 322 and the fourth conductive edge 376 of the fourth conductive layer 362. In such an example, the second conductive layer 322 can be electrically coupled to the fourth conductive layer 362, such that electric current can flow (e.g., flow illustrated with arrowhead 502) between the second conductive layer 322 and the fourth conductive layer 362. In some examples, electrical signals (e.g., related to imaging data, status information, etc.) can be transmitted through the second conductive layer 322 and/or the fourth conductive layer 362. In other examples, the second conductive layer 322 and/or the fourth conductive layer 362 may be coupled to a voltage source (e.g., ground) configured to maintain a substantially constant voltage on the second conductive layer 322 and/or the fourth conductive layer 362.

Portions of the second conductive retainer 480 can extend into the second opening 472 of the second attachment housing 452. For example, lower portions of the first conductive portion 482 and/or the second conductive portion 484 can be positioned to extend into the second opening 472 of the second attachment housing 452. In some examples, the first conductive portion 482 and/or the second conductive portion 484 can contact the second body portion 458, with the second body portion 458 applying a downward force to the first conductive portion 482 and/or the second conductive portion 484. In response to this force, the first conductive portion 482 and/or the second conductive portion 484 can flex outwardly. This outward flexion can cause lower portions of the first conductive portion 482 and/or the second conductive portion 484 to extend into the first channel 474 and/or the second channel 476. Additionally, the second body portion 458 can function to maintain the second conductive retainer 480 within the second retainer opening 390, thus ensuring that the second conductive retainer 480 remains in contact with the second conductive layer 322 and the fourth conductive layer 362.

To assist in attaching the second circuit board assembly 320 with respect to the fourth circuit board assembly 360, the first attachment structure 466 and the second attachment structure 470 can be attached to the second circuit board assembly 320 and the fourth circuit board assembly 360, respectively. For example, the first attachment structure 466 of the second attachment housing 452 can be attached to the second dielectric layer 324 of the second circuit board assembly 320. In this example, the first attachment structure 466 is illustrated as being at least partially embedded into the second dielectric layer 324. Similarly, in this example, the second attachment structure 470 can be attached to the fourth dielectric layer 364 of the fourth circuit board assembly 360, such as by being at least partially embedded into the fourth dielectric layer 364.

It will be appreciated that other methods of attachment are envisioned for attaching the second attachment housing 452 to the second circuit board assembly 320 and the fourth circuit board assembly 360. For example, the first attachment structure 466 and/or the second attachment structure 470 may comprise an adhesive (e.g., an epoxy, glue, etc.), such that the first attachment structure 466 can adhere to the second dielectric layer 324 while the second attachment structure 470 can adhere to the fourth dielectric layer 364. In another example, the first attachment structure 466 and/or the second attachment structure 470 can comprise fasteners (e.g., screws, bolts, clamps, etc.), such that the second attachment housing 452 can be attached (e.g., by threading attachment) to the second circuit board assembly 320 and the fourth circuit board assembly 360. In these examples, the second attachment housing 452 can function to attach the second circuit board assembly 320 and the fourth circuit board assembly 360, such that inadvertent movement and/or separation is substantially limited e.g., mitigated). Further, although not shown, the first attachment housing 402 and the second attachment housing 452 may be coupled together (e.g., and formed as a unitary structure), to apply compressive force to the circuit board assemblies 300, 320, 340, and 360 and the insulating layer. For example, on an opposing side of the first data communication component 202 (e.g., opposite the side depicting in FIG. 4), one or more braces or other structures may couple the first attachment housing 402 to the second attachment house 452.

Figure 6:
FIG. 6 illustrates an example plot of attenuation of an example data communication component having a design as provided for herein.
Figure 7:
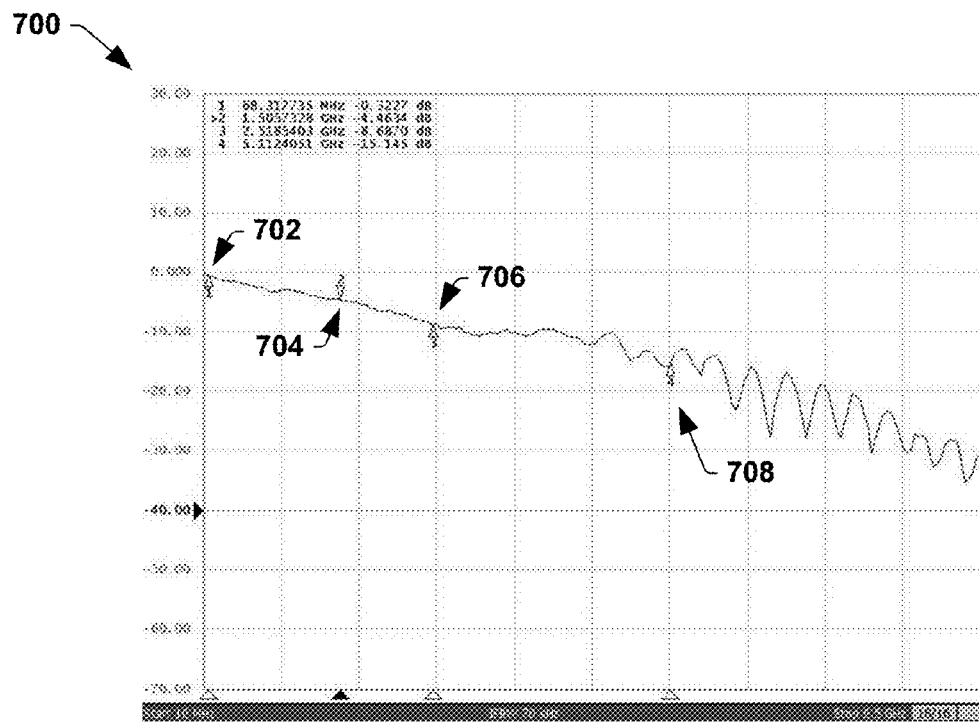
FIG. 7 illustrates an example plot of attenuation of a data communication component having a conventional design.

Turning to FIGS. 6 and 7, experimental results are provided to illustrate some of the benefits of a data communication component 202 (e.g., antenna) having a design as described herein over conventional designs. The x-axis of respective plots 600 and 700 represents the frequency (in Hertz) of signals and the y-axis represents the attenuation (in decibels) of the signals. More particularly, FIG. 6 illustrates the attenuation of signals across a 1 meter data communication component 202 having a design as described herein, and FIG. 7 illustrates the attenuation of signals across a 1 meter data communication component having a conventional design. The 1 meter length of the data communication component 202 is merely an example length for purposes of experimentation and thus the instant application is not intended to be limited to data communication components 202 of such length.

Referring to FIG. 6, the maximum attention of signals having a range of frequencies between about 10 megahertz (MHz) and 8.5 GHz gigahertz (GHz) is about negative 13 decibels. For example, the attenuation of a 68 MHz signal, as represented at a first point 602, is about +1.1 decibels. The attenuation of a 1.5 GHz signal, as represented at a second point 604, is about −0.05 decibels. The attenuation of a 2.5 GHz signal, as represented at a third point 606, is about −1.6 decibels. The attenuation of a 5.1 GHz signal, as represented at a fourth point 608, is about −5.8 decibels.

Turning to FIG. 7, the maximum attenuation of signals, having the same range of frequencies and transmitted through a data communication component having a conventional design, is about −35 decibels. For example, the attenuation of a 68 MHz signal, as represented at a first point 702, is about −0.3 decibels. The attenuation of a 1.5 GHz signal, as represented at a second point 704, is about −4.4 decibels. The attenuation of a 2.5 GHz signal, as represented as a third point 706, is about −8.7 decibels. The attenuation of a 5.1 GHz signal, as represented as a fourth point 708, is about −15.1 decibels. In comparing these attenuation measurements with the attenuation measurements of the data communication component having the design as described herein, it may be appreciated that the design as described herein has reduced attenuation levels in comparison with the conventional design, particularly at frequencies on the upper end of the range described herein.

It will be appreciated that in the examples illustrated herein, the first data communication component 202 comprises four circuit board assemblies, with the first circuit board assembly 300 and the second circuit board assembly 320 substantially end to end with the third circuit board assembly 340 and the fourth circuit board assembly 360. The first data communication component 202 is not limited to comprising the illustrated four circuit board assemblies, but, rather, may comprise any number (e.g., one or more) of circuit board assemblies, mounted in a similar manner as illustrated herein. In some examples, the first data communication component 202 can have a circumferential length of between about 1 meter to about 2 meters (e.g., such as for medical applications), or about 3 meters to about 4 meters (e.g., such as for security applications). However, other circumferential lengths are envisioned.

By providing the insulating layer 338 between (e.g., "sandwiched") opposing circuit board assemblies, electrical signals can be transmitted on opposing sides (e.g., a top surface and a bottom surface) of the insulating layer 338. The support structure 400 can function to attach the circuit board assemblies in an end to end manner, with the insulating layer 338 extending between opposing circuit board assemblies. As such, the first data communication component 202 can achieve a relatively longer circumferential length.

The words "example" and/or "exemplary" are used herein to mean serving as an example, instance, or illustration. Any aspect, design, etc. described herein as "example" and/or "exemplary" is not necessarily to be construed as advantageous over other aspects, designs, etc. Rather, use of these terms is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims may generally be construed to mean "one or more" unless specified otherwise or clear from context to be directed to a singular form. Also, at least one of A and B or the like generally means A or B or both A and B.

Although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated example implementations of the disclosure. Similarly, illustrated ordering(s) of acts is not meant to be limiting, such that different orderings comprising the same of different (e.g., numbers) of acts are intended to fall within the scope of the instant disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes", "having", "has", "with", or variants thereof are used in either the detailed description or the claims, such terms are intended to be inclusive in a manner similar to the term "comprising."

What is claimed is:

1. A computed tomography (CT) imaging modality comprising:
    a stator;
    a rotor configured to rotate relative to the stator;
    a radiation source coupled to the rotor and configured to emit radiation;
    a detector array coupled to the rotor and configured to detect at least some of the radiation; and
    a first data communication component coupled to the stator or the rotor for transmitting data between the stator and the rotor, the first data communication component comprising:
        a first circuit board assembly comprising a first conductive layer and a first dielectric layer;
        a second circuit board assembly comprising a second conductive layer and a second dielectric layer, the second circuit board assembly spaced apart from the first circuit board assembly, wherein the second conductive layer of the second circuit board assembly faces the first conductive layer of the first circuit board assembly; and
        an insulating layer disposed between the first conductive layer of the first circuit board assembly and the second conductive layer of the second circuit board assembly.

2. The CT imaging modality of claim 1, wherein the first data communication component extends circumferentially about an axis.

3. The CT imaging modality of claim 2, wherein the second circuit board assembly is disposed radially inwardly from the first circuit board assembly relative to the axis.

4. The CT imaging modality of claim 2, wherein the first dielectric layer is disposed radially outwardly from the first conductive layer relative to the axis.

5. The CT imaging modality of claim 2, wherein the second dielectric layer is disposed radially inwardly from the second conductive layer relative to the axis.

6. The CT imaging modality of claim 2, comprising a third circuit board assembly comprising a third conductive layer that is circumferentially aligned with the first conductive layer, and a third dielectric layer that is circumferentially aligned with the first dielectric layer.

7. The CT imaging modality of claim 6, wherein the first circuit board assembly is circumferentially spaced apart from the third circuit board assembly to define a first retainer opening between the first circuit board assembly and the third circuit board assembly.

8. The CT imaging modality of claim 7, wherein a first conductive edge of the first conductive layer defines a first side of the first retainer opening and a third conductive edge of the third conductive layer defines a second side of the first retainer opening.

9. The CT imaging modality of claim 8, comprising a first conductive retainer disposed within the first retainer opening, the first conductive retainer electrically coupled to the first conductive edge of the first conductive layer and the third conductive edge of the third conductive layer.

10. The CT imaging modality of claim 1, comprising a second data communication component that is configured to form an electromagnetic coupling with the first data communication component, the second data communication component coupled to:
    the stator when the first data communication component is coupled to the rotor; or
    the rotor when the first data communication component is coupled to the stator.

11. A computed tomography (CT) imaging modality comprising:
    a stator;
    a rotor configured to rotate relative to the stator;
    a radiation source coupled to the rotor and configured to emit radiation;
    a detector array coupled to the rotor and configured to detect at least some of the radiation; and
    a first data communication component coupled to the stator or the rotor for transmitting data between the stator and the rotor, the first data communication component comprising:
        a first circuit board assembly comprising:
            a first conductive layer; and
            a first dielectric layer, the first dielectric layer having:
                a first surface in contact with the first conductive layer;
                a second surface substantially parallel to the first surface; and
                a first lateral surface defining a first end of the first dielectric layer and extending between the first surface and the second surface, wherein a first conductive edge of the first conductive layer extends from the first surface towards the second surface along the first lateral surface;
        a second circuit board assembly comprising a second conductive layer and a second dielectric layer, the second circuit board assembly spaced apart from the first circuit board assembly, wherein the second conductive layer of the second circuit board assembly faces the first conductive layer of the first circuit board assembly; and an insulating layer disposed between the first conductive layer of the first circuit board assembly and the second conductive layer of the second circuit board assembly.

12. The CT imaging modality of claim 11, comprising a first conductive retainer disposed in proximity to the first lateral surface of the first dielectric layer, the first conductive retainer electrically coupled to the first conductive edge of the first conductive layer.

13. The CT imaging modality of claim 11, wherein the second dielectric layer has:
   a third surface in contact with the second conductive layer;
   a fourth surface substantially parallel to the second surface; and
   a second lateral surface defining a second end of the second dielectric layer and extending between the third surface and the fourth surface, wherein a second conductive edge of the second conductive layer extends from the third surface towards the fourth surface along the second lateral surface.

14. The CT imaging modality of claim 13, comprising a second conductive retainer disposed in proximity to the second lateral surface of the second dielectric layer, the second conductive retainer electrically coupled to the second conductive edge of the second conductive layer.

15. The CT imaging modality of claim 11, wherein the first lateral surface of the first dielectric layer defines a first angle with respect to the first surface, the first angle less than about 90 degrees.

16. A computed tomography (CT) imaging modality comprising:
   a stator;
   a rotor configured to rotate relative to the stator;
   a radiation source coupled to the rotor and configured to emit radiation;
   a detector array coupled to the rotor and configured to detect at least some of the radiation; and
   a first data communication component coupled to the stator or the rotor for transmitting data between the stator and the rotor, the first data communication component comprising:
      a first circuit board assembly comprising a first conductive layer and a first dielectric layer;
      a second circuit board assembly comprising a second conductive layer and a second dielectric layer, the second circuit board assembly spaced apart from the first circuit board assembly, wherein the second conductive layer of the second circuit board assembly faces the first conductive layer of the first circuit board assembly;
      an insulating layer disposed between the first conductive layer of the first circuit board assembly and the second conductive layer of the second circuit board assembly; and
      a support structure circumferentially surrounding one or more of the first circuit board assembly, the second circuit board assembly, or the insulating layer, the support structure configured to maintain a relative position of the first circuit board assembly, the second circuit board assembly, and the insulating layer.

17. The CT imaging modality of claim 16, comprising:
   a third circuit board assembly comprising a third conductive layer and a third dielectric layer; and
   a fourth circuit board assembly comprising a fourth conductive layer and a fourth dielectric layer, the fourth circuit board assembly spaced apart from the third circuit board assembly, wherein the fourth conductive layer faces the third conductive layer,
   wherein the insulating layer is disposed between the third conductive layer and the fourth conductive layer.

18. The CT imaging modality of claim 17, wherein the support structure comprises a first attachment housing, the first attachment housing configured to attach the first circuit board assembly to the third circuit board assembly.

19. The CT imaging modality of claim 18, wherein the support structure comprises a second attachment housing, the second attachment housing configured to attach the second circuit board assembly to the fourth circuit board assembly.

20. The CT imaging modality of claim 17, wherein:
   the first conductive layer is electrically coupled to the third conductive layer; and
   the second conductive layer is electrically coupled to the fourth conductive layer.

* * * * *